United States Patent
Jadhav

(10) Patent No.: US 9,687,293 B2
(45) Date of Patent: *Jun. 27, 2017

(54) DEPLOYMENT MECHANISM FOR SURGICAL INSTRUMENTS

(71) Applicant: COVIDIEN LP, Mansfield, MA (US)

(72) Inventor: Amarsinh D. Jadhav, Dist-Sangli (IN)

(73) Assignee: COVIDIEN LP, Mansfield, MA (US)

( * ) Notice: Subject to any disclaimer, the term of this patent is extended or adjusted under 35 U.S.C. 154(b) by 282 days.

This patent is subject to a terminal disclaimer.

(21) Appl. No.: 14/542,796

(22) Filed: Nov. 17, 2014

(65) Prior Publication Data

US 2016/0135863 A1 May 19, 2016

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01); *A61B 2018/1422* (2013.01); *A61B 2018/1455* (2013.01); *A61B 2018/1467* (2013.01); *A61B 2018/1475* (2013.01)

(58) Field of Classification Search
CPC ..... A61B 17/00; A61B 18/00; A61B 18/1445; A61B 2018/00083; A61B 2018/00214; A61B 2018/1253; A61B 2018/126; A61B 2018/1455; A61B 2018/1467; A61B 2018/1475
See application file for complete search history.

(56) References Cited

U.S. PATENT DOCUMENTS

| 5,312,391 A | 5/1994 | Wilk |
| 5,318,589 A | 6/1994 | Lichtman |
| 5,324,254 A | 6/1994 | Phillips |
| 5,401,274 A | 3/1995 | Kusunoki |

(Continued)

FOREIGN PATENT DOCUMENTS

| EP | 1885270 A1 | 2/2008 |
| EP | 2679185 A1 | 1/2014 |

(Continued)

OTHER PUBLICATIONS

European Search Report issued in corresponding application No. 15191338.1 on Jan. 11, 2016.

*Primary Examiner* — Daniel Fowler

(57) ABSTRACT

A surgical instrument includes a housing, an energizable member, a proximal hub, and a deployment mechanism. The energizable member is movable between a storage position and a deployed position. The proximal hub is disposed within the housing, coupled to the energizable member, and translatable relative to the housing along a translation axis to deploy the energizable member. The deployment mechanism is configured to selectively translate the proximal hub and includes an actuator movable along a surface of the housing that extends in non-parallel orientation relative to the translation axis. The actuator is operably coupled to the proximal hub and is movable along the surface of the housing in non-parallel orientation relative to the translation axis between a proximal position and a distal position to translate the proximal hub along the translation axis and move the energizable member between the storage position and the deployed position.

15 Claims, 6 Drawing Sheets

(56) References Cited

U.S. PATENT DOCUMENTS

| | | |
|---|---|---|
| 5,445,638 A | 8/1995 | Rydell et al. |
| 5,458,598 A | 10/1995 | Feinberg et al. |
| 5,556,397 A | 9/1996 | Long et al. |
| 5,735,873 A | 4/1998 | MacLean |
| 5,792,164 A | 8/1998 | Lakatos et al. |
| 5,893,863 A | 4/1999 | Yoon |
| 5,908,432 A | 6/1999 | Pan |
| 5,919,202 A | 7/1999 | Yoon |
| 6,113,596 A | 9/2000 | Hooven et al. |
| 6,156,009 A | 12/2000 | Grabek |
| 6,190,386 B1 | 2/2001 | Rydell |
| 6,270,497 B1 | 8/2001 | Sekino et al. |
| 6,299,625 B1 | 10/2001 | Bacher |
| 6,387,094 B1 | 5/2002 | Eitenmuller |
| 6,551,313 B1 | 4/2003 | Levin |
| 6,679,882 B1 | 1/2004 | Kornerup |
| 6,808,525 B2 | 10/2004 | Latterell et al. |
| 6,942,662 B2 | 9/2005 | Goble et al. |
| 7,033,356 B2 | 4/2006 | Latterell et al. |
| 7,063,699 B2 | 6/2006 | Hess et al. |
| 7,128,254 B2 | 10/2006 | Shelton, IV et al. |
| 7,232,440 B2 | 6/2007 | Dumbauld et al. |
| 7,367,976 B2 | 5/2008 | Lawes et al. |
| 7,402,162 B2 | 7/2008 | Ouchi |
| 7,445,621 B2 | 11/2008 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| 7,758,577 B2 | 7/2010 | Nobis et al. |
| 7,815,636 B2 | 10/2010 | Ortiz |
| 7,819,872 B2 | 10/2010 | Johnson et al. |
| 8,257,352 B2 | 9/2012 | Lawes et al. |
| 8,353,437 B2 | 1/2013 | Boudreaux |
| 2002/0049442 A1 | 4/2002 | Roberts et al. |
| 2004/0087940 A1 | 5/2004 | Jahns et al. |
| 2004/0236326 A1 | 11/2004 | Schulze et al. |
| 2005/0107784 A1 | 5/2005 | Moses et al. |
| 2005/0187547 A1 | 8/2005 | Sugi |
| 2006/0074416 A1* | 4/2006 | Hushka ............ A61B 18/1445 606/51 |
| 2008/0215050 A1 | 9/2008 | Bakos |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2012/0330351 A1 | 12/2012 | Friedman et al. |
| 2014/0276797 A1 | 9/2014 | Batchelor et al. |

FOREIGN PATENT DOCUMENTS

| | | |
|---|---|---|
| WO | 2006/104835 A1 | 10/2006 |
| WO | 2014/123621 A1 | 8/2014 |

* cited by examiner

DEPLOYMENT MECHANISM FOR SURGICAL INSTRUMENTS

BACKGROUND

Technical Field

The present disclosure relates to surgical instruments and, more particularly, to a deployment mechanism for deploying, e.g., actuating, component(s) of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the instrument, additional deployment structures or deployment structures capable of actuating more than one component are required. However, multiple deployment structures and/or combined deployment structures may be limited by spatial constraints within the housing of the instrument, functional constraints of the components (e.g., where a combined deployment structure imparts additional force requirements for deploying one or more of the components coupled thereto), and/or may overly complicate the operable components of the instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including a housing, an energizable member, a proximal hub, and a deployment mechanism. The energizable member is movable between a storage position and a deployed position. The proximal hub is disposed within the housing and is coupled to the energizable member. The proximal hub is selectively translatable relative to the housing along a translation axis to move the energizable member between the storage position and the deployed position. The deployment mechanism is configured to selectively translate the proximal hub to thereby deploy and retract the energizable member. The deployment mechanism including an actuator movable along a surface of the housing. The surface of the housing extends in non-parallel orientation relative to the translation axis such that the actuator is movable along the surface of the housing in non-parallel orientation relative to the translation axis. More specifically, the actuator is operably coupled to the proximal hub and is movable along the surface of the housing between a proximal position and a distal position to translate the proximal hub along the translation axis and move the energizable member between the storage position and the deployed position.

In an aspect of the present disclosure, the deployment mechanism further includes a post extending from the proximal hub in generally perpendicular orientation relative to the translation axis, and a sleeve slidably disposed about the post. The sleeve includes the actuator extending therefrom. The sleeve is slid about the post upon movement of the actuator along the surface of the housing.

In another aspect of the present disclosure, the deployment mechanism further includes a biasing member disposed about the post and positioned between the sleeve and the proximal hub. The biasing member is configured to bias the sleeve away from the proximal hub.

In yet another aspect of the present disclosure, the surface of the housing defines a proximal end and a distal end and is configured such that the distal end of the surface of the housing is disposed in closer proximity to the translation axis as compared to the proximal end of the surface of the housing. In this configuration, the biasing member thus biases the energizable member towards the storage position.

In still another aspect of the present disclosure, a portion of the sleeve extends through a slot defined within the housing. Further, the slot may define an enlarged portion at an end thereof that is configured to permit the sleeve to further extend through the slot under the bias of the biasing member to lock the actuator at the end of the slot. With the actuator locked at the end of the slot, the energizable member is locked in the deployed condition.

In still yet another aspect of the present disclosure, the surgical instrument further includes a shaft extending distally from the housing and having an end effector disposed at a distal end thereof. In such aspects, in the deployed position, at least a portion of the energizable member extends distally from the end effector assembly.

In another aspect of the present disclosure, an insulative sleeve is coupled to the proximal hub. In such aspects, translation of the proximal hub along the translation axis moves the insulative sleeve between a storage position and a deployed position. In the deployed position, the insulative sleeve is at least partially disposed about the end effector assembly.

In still another aspect of the present disclosure, the end effector assembly includes first and second jaw members. One or both of the first and second jaw members is movable relative to the other between a spaced-apart position and an approximated position for grasping tissue therebetween.

In yet another aspect of the present disclosure, the end effector assembly is adapted to connect to a source of bipolar energy for treating tissue grasped between the first and second jaw members, while the energizable member is adapted to connect to a source of monopolar energy for treating tissue adjacent the energizable member.

Another surgical instrument provided in accordance with the present disclosure includes a housing, a shaft extending distally from the housing, an end effector assembly disposed at a distal end of the shaft, a deployable assembly, and an actuator. The deployable assembly includes an insulative sleeve, an energizable member, and a proximal hub. The deployable assembly is transitionable between a storage condition and a deployed condition, wherein, in the deployed condition, the insulative sleeve is at least partially disposed about the end effector assembly and at least a portion of the energizable member extends distally from the end effector assembly. The proximal hub is disposed within the housing and is coupled to both the insulative sleeve and the energizable member. The proximal hub is selectively translatable relative to the housing along a translation axis to transition the deployable assembly between the storage condition and the deployed condition. The actuator is coupled to the proximal hub for selectively deploying the deployable assembly. The actuator is movable relative to the housing along a path that extends in non-parallel orientation relative to the translation axis. More specifically, the actuator is movable between an un-actuated position corresponding to the storage condition of the deployable assembly, wherein the actuator is disposed at a proximal end of a portion of the housing and wherein the actuator is spaced-apart from the translation axis a first distance, and an actuated position corresponding to the deployed condition of the deployable assembly, wherein the actuator is disposed at a distal end of the portion of the housing and wherein the actuator is spaced-apart from the translation axis a second distance that is smaller than the first distance.

In an aspect of the present disclosure, the surgical instrument further includes a post extending from the proximal hub and a sleeve slidably disposed about the post. The sleeve includes the actuator extending therefrom and is slidable about the post upon movement of the actuator relative to the housing.

In another aspect of the present disclosure, a biasing member is disposed about the post and positioned between the sleeve and the proximal hub. The biasing member is configured to bias the sleeve away from the proximal hub, thereby biasing the actuator towards the un-actuated position.

In still another aspect of the present disclosure, the portion of the housing extends in non-parallel orientation relative to the translation axis. The actuator is slidable along the surface defined by this portion of the housing.

In yet another aspect of the present disclosure, a lock mechanism configured to lock the actuator in the actuated position corresponding to the deployed condition of the deployable assembly is provided.

In still yet another aspect of the present disclosure, the end effector assembly includes first and second jaw members, either or both of which are movable relative to the other between a spaced-apart position and an approximated position for grasping tissue therebetween.

In another aspect of the present disclosure, the end effector assembly is adapted to connect to a source of bipolar energy for treating tissue grasped between the first and second jaw members, while the energizable member is adapted to connect to a source of monopolar energy for treating tissue adjacent the energizable member.

Another surgical instrument provided in accordance with the present disclosure includes a housing, a shaft extending distally from the housing, an end effector assembly disposed at a distal end of the shaft, a deployable assembly, and a deployment mechanism. The deployable assembly includes an energizable member and a proximal hub and is transitionable between a storage condition and a deployed condition. In the deployed condition, at least a portion of the energizable member extends distally from the end effector assembly. The proximal hub is disposed within the housing and is coupled to the energizable member. The proximal hub is selectively translatable relative to the housing along a translation axis to transition the deployable assembly between the storage condition and the deployed condition. The deployment mechanism is configured to selectively deploy the deployable assembly and includes a post, a sleeve, an actuator, and a biasing member. The post extends from the proximal hub in generally perpendicular orientation relative to the translation axis. The sleeve is slidably disposed about the post in a direction generally perpendicular relative to the translation axis. A portion of the sleeve extends through a slot defined within the housing. The actuator is coupled to the sleeve and positioned exteriorly of the housing. The actuator is slidable along a surface of the housing in a non-parallel and non-perpendicular direction relative to the translation axis. The actuator is movable along such a path relative to the housing between an un-actuated position corresponding to the storage condition of the deployable assembly, wherein the actuator is spaced-apart from the translation axis a first distance, and an actuated position corresponding to the deployed condition of the deployable assembly, wherein the actuator is spaced-apart from the translation axis a second distance that is smaller than the first distance. The biasing member is disposed about the post and positioned between the sleeve and the proximal hub such that the biasing member compresses as the actuator moves towards the actuated position, thereby biasing the actuator towards the un-actuated position.

In an aspect of the present disclosure, the slot defined within the housing includes an enlarged distal portion. In such aspects, when the actuator is disposed in the actuated position, the sleeve is positioned adjacent the enlarged distal portion of the slot such that the biasing member urges the sleeve to extend further through the slot, thereby locking the actuator in the actuated position corresponding to the deployed condition of the deployable assembly.

In another aspect of the present disclosure, the end effector assembly is adapted to connect to a source of bipolar energy for treating tissue with bipolar energy, while the energizable member is adapted to connect to a source of monopolar energy for treating tissue with monopolar energy.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
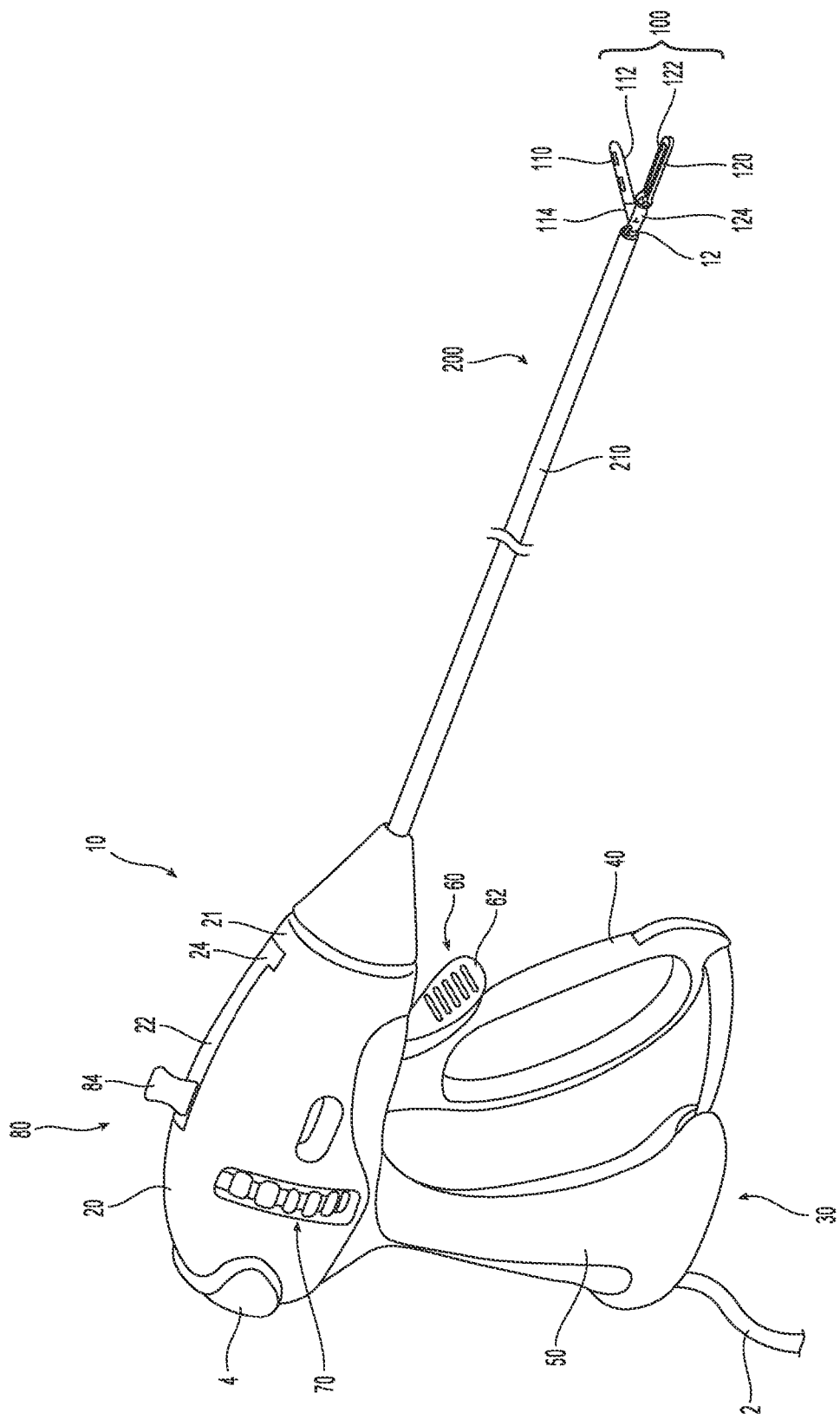
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying one or more assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a trigger assembly 60, a rotating assembly 70, a deployment mechanism 80, an end effector assembly 100, and a monopolar assembly 200. Forceps 10 further includes a shaft 12 having a distal end configured to mechanically engage end effector assembly 100 and a proximal end that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one of the electrically-conductive surfaces 112, 122 (FIG. 2A) of jaw members 110, 120, respectively, of end effector assembly 100, e.g., upon activation of activation switch 4 in a bipolar mode. One or more of the wires (not shown) of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10.

Figure 2A:
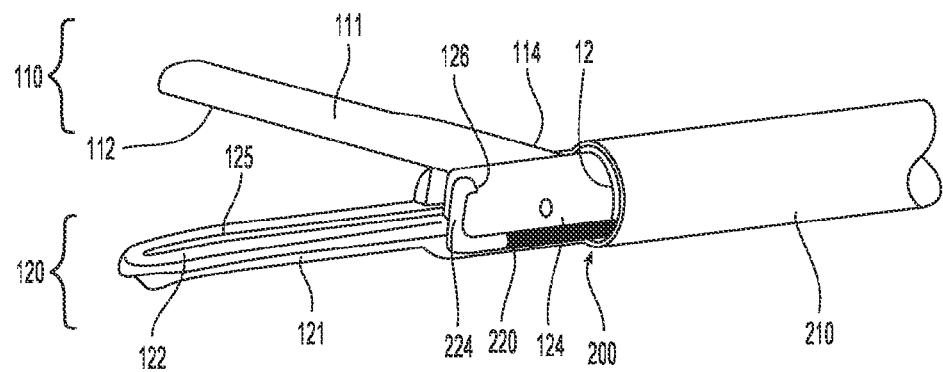
FIG. 2A is an enlarged, front, perspective view of an end effector assembly of the forceps of FIG. 1, wherein jaw members of the end effector assembly are disposed in a spaced-apart position and wherein a monopolar assembly is disposed in a storage condition.
Figure 2B:
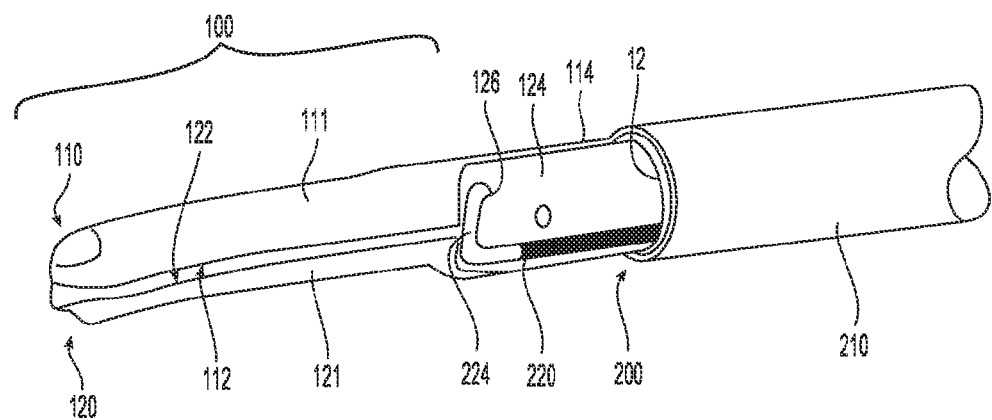
FIG. 2B is an enlarged, front, perspective view of the end effector assembly of FIG. 2A, wherein the jaw members are disposed in an approximated position and wherein the monopolar assembly is disposed in the storage condition.
Figure 2C:
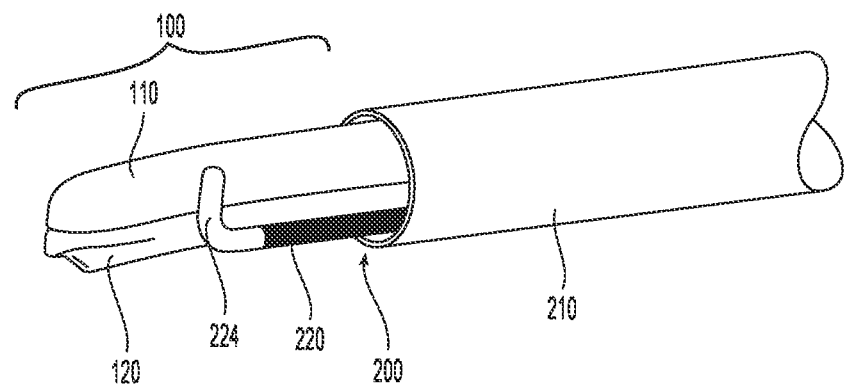
FIG. 2C is an enlarged, front, perspective view of the end effector assembly of FIG. 2A, wherein the jaw members are disposed in the approximated position and wherein the monopolar assembly is transitioning from the storage condition to a deployed condition.

Referring to FIGS. 2A-2B, end effector assembly 100 is attached at the distal end of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2A) and an approximated position (FIG. 2B) for grasping tissue between surfaces 112, 122. One or both of surfaces 112, 122 are adapted to connect to a source of energy (not explicitly shown), e.g., via the wires (not shown) of cable 2 (FIG. 1) and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of a knife (not shown) therethrough, e.g., upon actuation of a trigger 62 of trigger assembly 60, to cut tissue grasped between jaw members 110, 120.

Figure 2D:
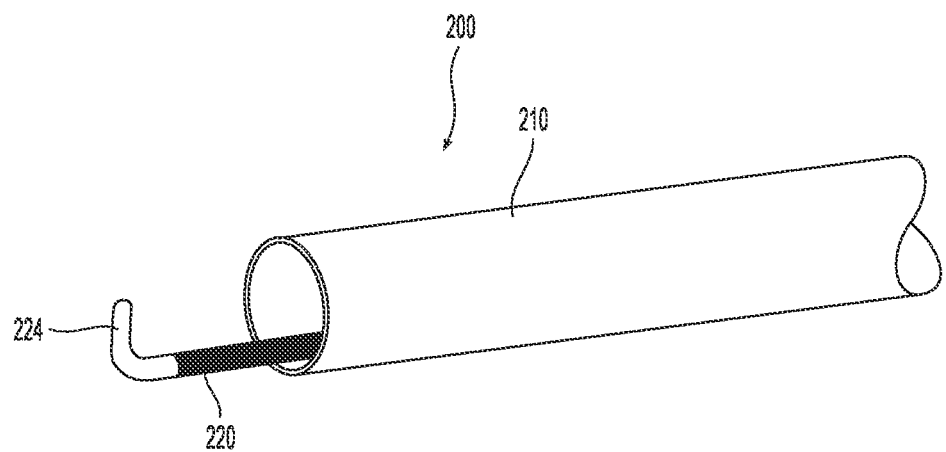
FIG. 2D is an enlarged, front, perspective view of the end effector assembly of FIG. 2A, wherein the monopolar assembly is disposed in the deployed condition.
Figure 3A:
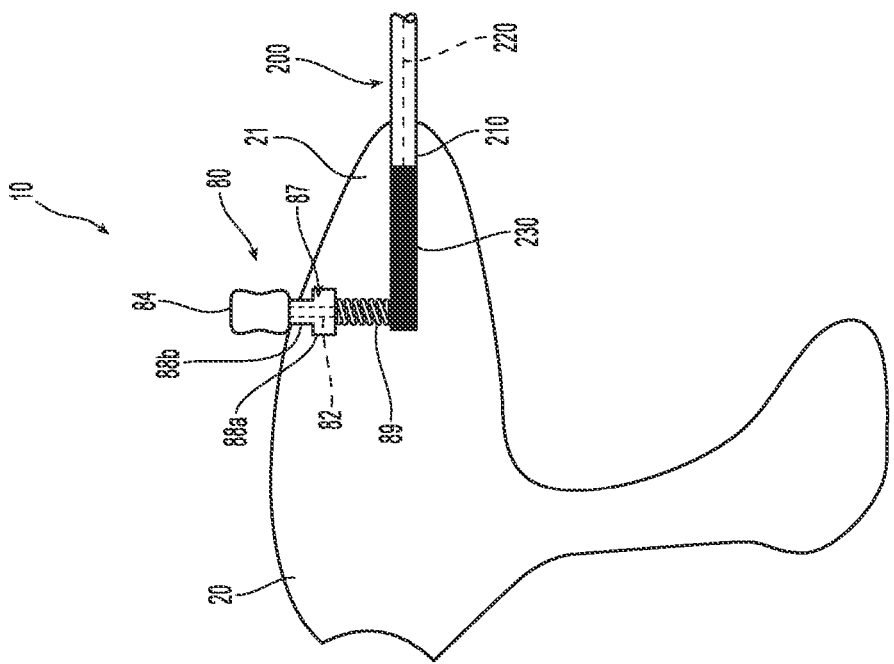
FIG. 3A is a side view of the proximal end of the forceps of FIG. 1 with a portion of the housing and internal components thereof removed to unobstructively illustrate the proximal end of the monopolar assembly and a deployment mechanism for deploying the monopolar assembly, wherein the deployment mechanism is disposed in an un-actuated condition corresponding to the storage condition of the monopolar assembly.
Figure 3B:
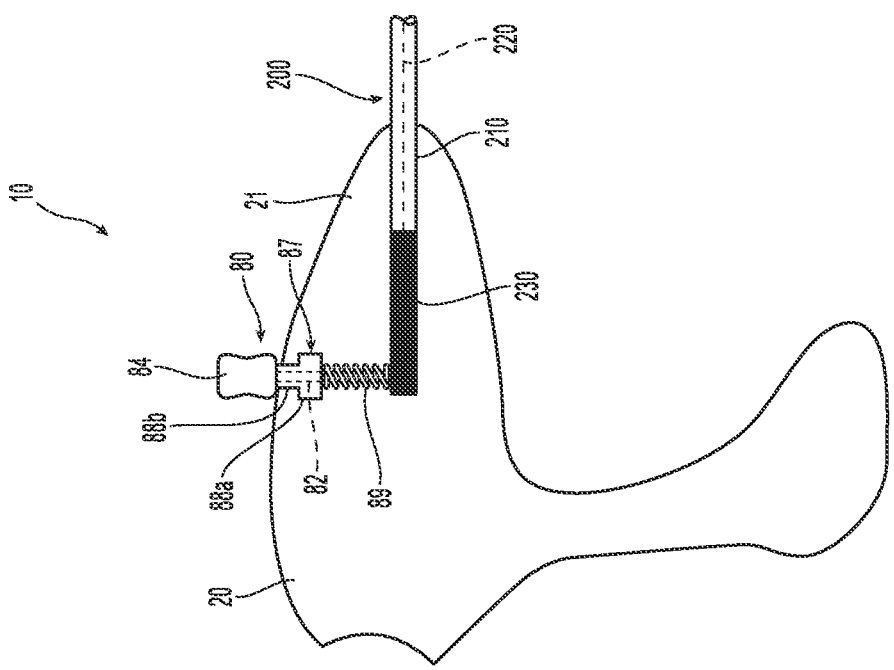
FIG. 3B is a side view of the proximal end of the forceps of FIG. 1 with a portion of the housing and internal components thereof removed to unobstructively illustrate the proximal end of the monopolar assembly and the deployment mechanism, wherein the deployment mechanism is disposed in a partially-actuated condition corresponding to the monopolar assembly being disposed between the storage condition and the deployed condition.
Figure 3C:
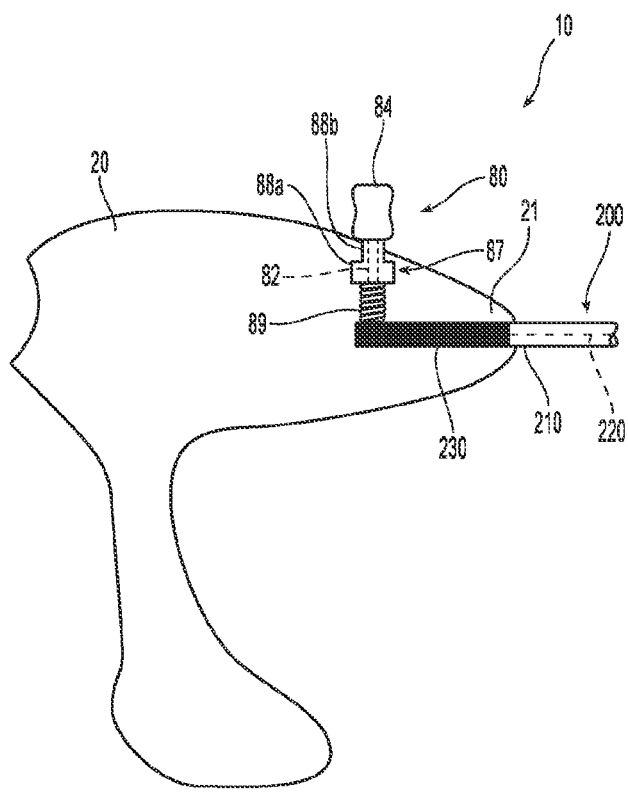
FIG. 3C is a side view of the proximal end of the forceps of FIG. 1 with a portion of the housing and internal components thereof removed to unobstructively illustrate the proximal end of the monopolar assembly and the deployment mechanism, wherein the deployment mechanism is disposed in an actuated condition corresponding to the deployed condition of the monopolar assembly.
Figure 4A:
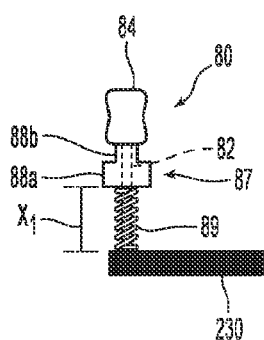
FIG. 4A is a side view of the deployment mechanism disposed in the un-actuated condition.
Figure 4B:
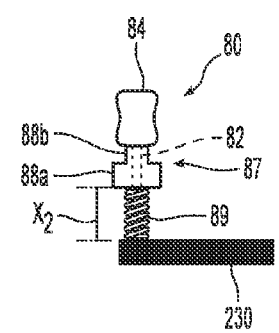
FIG. 4B is a side view of the deployment mechanism disposed in a partially-actuated condition.
Figure 4C:
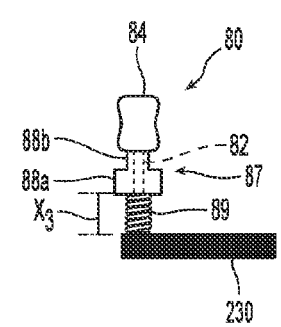
FIG. 4C is a side view of the deployment mechanism disposed in the actuated condition.

Referring to FIGS. 1-2D, monopolar assembly 200 includes an insulative sleeve 210, an energizable rod member 220, and a proximal hub 230 (FIG. 3A). Insulative sleeve 210 is slidably disposed about shaft 12 and is selectively movable about and relative to shaft 12 and end effector assembly 100 between a storage position (FIGS. 2A and 2B), wherein insulative sleeve 210 is disposed proximally of end effector assembly 100, and a deployed position (FIG. 2D), wherein insulative sleeve 210 is substantially disposed about end effector 100 so as to electrically insulate surfaces 112, 122 of jaw members 110, 120, respectively. With momentary reference to FIG. 3A, proximal hub 230 is engaged to insulative sleeve 210 at the proximal end of insulative sleeve 210 and also engages the proximal end of energizable rod member 220. As detailed below, deployment mechanism 80 is selectively actuatable to translate proximal hub 230 along a translation axis through housing 20 and relative to shaft 12 to thereby move monopolar assembly 200 between its storage and deployed conditions (FIGS. 2B and 2D, respectively). The translation axis may be parallel with an axis defined by shaft 12, may be coaxial with the axis of shaft 12, or may be non-parallel relative thereto.

Referring again to FIGS. 1-2D, energizable rod member 220 extends from proximal hub 230 (FIG. 3A), through sleeve 210, and distally therefrom, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1) in a monopolar mode, for treating tissue in a monopolar mode of operation. Energizable rod member 220 is movable between a storage position (FIG. 2B) and a deployed position (FIG. 2D). In the storage position (FIG. 2B), distal tip 224 of rod member 220 is disposed within an insulated groove 126 defined within proximal flange 124 of jaw member 120, although other configurations are also contemplated. Insulated groove 126 electrically-insulates distal tip 224 of rod member 220 from electrically-conductive surfaces 112, 122 of jaw members 110, 120, respectively, and from surrounding tissue when disposed in the storage position. Alternatively, distal tip 224 of rod member 220 may only be insulated from surface 112. In such configurations, distal tip 224 of rod member 220 is capable of being energized to the same polarity as surface 122.

In the deployed position (FIG. 2D), distal tip 224 of rod member 220 of monopolar assembly 200 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode. Distal tip 224 may be hook-shaped (as shown), or may define any other suitable configuration, e.g., linear, ball, circular, angled, etc.

Insulative sleeve 210 and rod member 220 of monopolar assembly 200 are coupled to one another via proximal hub 230 (FIG. 3A), as will be described in greater detail below, such that insulative sleeve 210 and rod member 220 move in concert with one another, e.g., move together in simultaneous or nearly-simultaneous fashion, between their storage positions (FIGS. 2A and 2B), collectively the storage condition of monopolar assembly 200, and their deployed positions (FIG. 2D), collectively the deployed condition of monopolar assembly 200, upon selective translation of proximal hub 230 through housing 20 and relative to shaft 12 (see FIG. 1).

With reference again to FIG. 1, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) disposed within housing 20 that, together, mechanically cooperate to impart movement of jaw members 110, 120 between the spaced-apart position (FIG. 2A), corresponding to the initial position of movable handle 40, and the approximated position (FIG. 2B), corresponding to the compressed position of movable handle 40. Any suitable drive assembly for this purpose may be provided.

Trigger assembly 60 includes trigger 62 that is operably coupled to a knife (not shown). Trigger 62 of trigger assembly 60 is selectively actuatable to advance the knife from a retracted position, wherein the knife is disposed proximally of jaw members 110, 120, to an extended position, wherein the knife extends at least partially between jaw members 110, 120 and through knife channel(s) 125 (FIG. 2A) to cut tissue grasped between jaw members 110, 120.

Referring to FIGS. 1 and 3A-5C, deployment mechanism 80 is configured for selectively translating proximal hub 230 relative to housing 20 and shaft 12 to thereby transition monopolar assembly 200 between its storage condition (FIGS. 2A and 2B) and its deployed condition (FIG. 2D). Deployment mechanism 80 generally includes a post 82, an actuator 84, a sleeve 87, and a biasing member 89. Post 82 is secured to and extends from proximal hub 230 in generally perpendicular orientation relative thereto, although other configurations are also contemplated. Sleeve 87 is slidably disposed about post 82 and includes a first end defining a relatively large-diameter portion 88a and a second end defining a relatively small-diameter portion 88b. Actuator 84 is secured to the second end of sleeve 87. More specifically, the second end of sleeve 87 extends through a slot 22 defined within housing 20 such that actuator 84 is positioned exteriorly of housing 20. Actuator 84 is configured to be manually manipulated by a user, e.g., translated along slot 22 of housing 20, to transition deployment mechanism 80 between an un-actuated condition (FIGS. 3A, 4A, and 5A) and an actuated condition (FIGS. 3C, 4C, and 5C) to thereby transition monopolar assembly 200 between the storage condition (FIGS. 2A and 2B) and the deployed condition (FIG. 2D), respectively. Biasing member 89 is disposed about post 82 between sleeve 87 and proximal hub 230 to bias sleeve 87 away from proximal hub 230 (FIGS. 3A and 4A), the importance of which is detailed below.

Continuing with reference to FIGS. 1 and 3A-5C, the portion 21 of housing 20 adjacent deployment mechanism 80 extends in non-parallel orientation relative to the axis of translation of proximal hub 230, e.g., the axis along which proximal hub 230 is translated to deploy monopolar assembly 200. More specifically, the proximal end of the portion 21 of housing 20 is further-spaced from the axis of translation of proximal hub 230 as compared to the distal end of the portion 21 of housing 20. As a result of this configuration, as actuator 84 is translated distally along slot 22 and the exterior surface of housing 20 to deploy monopolar assembly 200, sleeve 87 is urged to slide about post 82 towards proximal hub 230, e.g., in a perpendicular direction relative to the translation axis, thereby compressing biasing member 89. On the other hand, upon return of actuator 84 proximally along slot 22 and the exterior surface of housing 20 to return monopolar assembly 200 to the storage condition, sleeve 87 is urged to slide about post 82 away from proximal hub 230, e.g., in a perpendicular direction relative to the translation axis, under the bias of biasing member 89. Thus, with actuator 84 disposed in a proximal-most position, corresponding to the un-actuated condition of deployment mechanism 80, biasing member 89 defines a length "$X_1$" (FIG. 4A); with actuator 84 disposed in an intermediate position, corresponding to a partially-actuated condition of deployment mechanism 80, biasing member 89 is compressed to a length "$X_2$" (FIG. 4B) that is smaller than length "$X_1$;" and with actuator 84 disposed in a distal-most position, corresponding to the actuated condition of deployment mechanism 80, biasing member 89 is further compressed to a length "$X_3$" (FIG. 4C) that is smaller than length "$X_2$." As a result of this configuration, actuator 84 is biased proximally relative to slot 22 of housing 20, e.g., towards the un-actuated condition of deployment mechanism 80, thereby biasing monopolar assembly 200 towards the storage condition. In order to achieve the above-noted non-parallel configuration, the portion 21 of housing 20 may be curved, angled, or otherwise configured to extend in non-parallel orientation relative to the axis of translation of proximal hub 230.

Figure 5C:
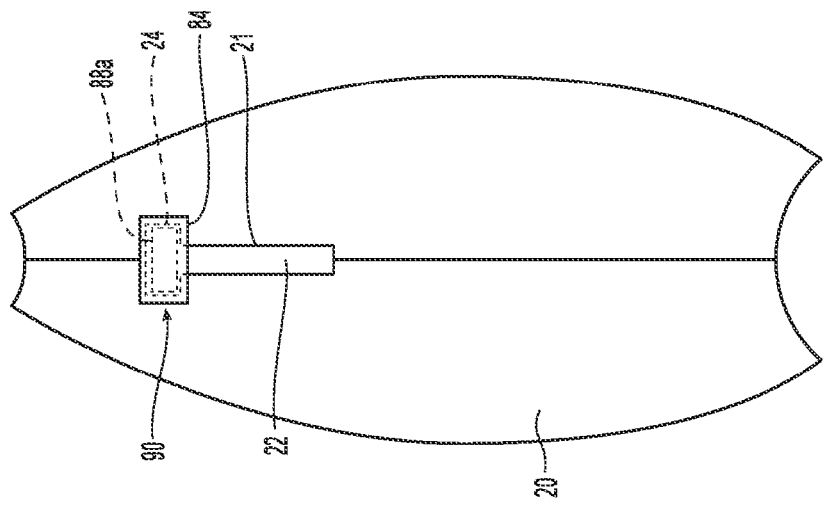
FIG. 5C is a top view of the housing of the forceps of FIG. 1 with the deployment mechanism disposed in the actuated condition.
Figure 5B:
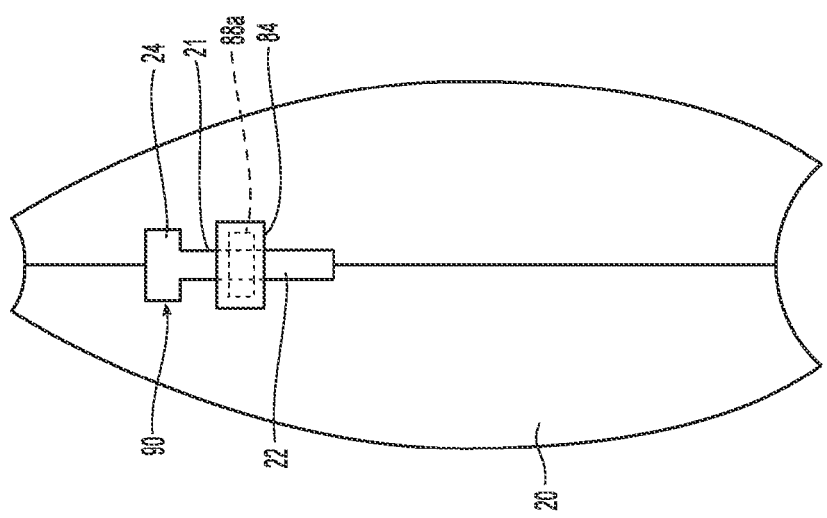
FIG. 5B is a top view of the housing of the forceps of FIG. 1 with the deployment mechanism disposed in a partially-actuated condition.
Figure 5A:
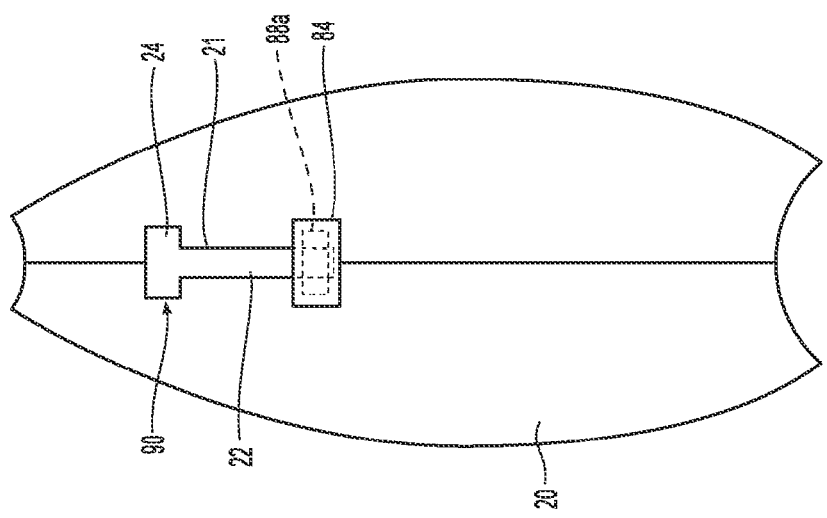
FIG. 5A is a top view of the housing of the forceps of FIG. 1 with the deployment mechanism disposed in the un-actuated condition.

With continued reference to FIGS. 1 and 3A-5C, and with particular reference to FIGS. 5A-5C, a lock mechanism 90 may also be provided to lock monopolar assembly 200 in the deployed condition against the bias of biasing member 89, once the actuated condition of deployment mechanism 80 has been achieved. Lock mechanism 90 is provided via an enlarged distal portion 24 of slot 22. Enlarged distal portion 24 is disposed at the distal end of slot 22 and is sufficiently large so as to permit passage of the relatively large-diameter portion 88a of sleeve 87 therethrough. The remainder of slot 22, on the other handle, is sufficiently large so as to permit passage of the relatively small-diameter portion 88b of sleeve 87 therethrough but sufficiently small so as to inhibit passage of the relatively large-diameter portion 88a of sleeve 87 therethrough. As a result, prior to actuator 84 reaching the enlarged distal portion 24 of slot 22, e.g., prior to deployment mechanism 80 reaching the actuated condition, biasing member 89 acts to urge the relatively large-diameter portion 88a of sleeve 87 away from proximal hub 230 and into contact with the interior surface of housing 20 adjacent slot 22. However, upon reaching the enlarged distal portion 24 of slot 22, the relatively large-diameter portion 88a of sleeve 87 is no longer restrained via housing 20 but, rather, is urged under the bias of biasing member 89 further from proximal hub 230, at least partially through enlarged distal portion 24 of slot 22. In other words, the additional clearance provided by enlarged distal portion 24 of slot 22 redirects the bias of biasing member 89 from biasing actuator 84 proximally to instead bias actuator 84 towards a locked condition wherein actuator 84 is locked in position due to the positioning of the relatively large-diameter portion 88a of sleeve 87 within enlarged distal portion 24 of slot 22. In order to unlock actuator 84, actuator 84 is urged towards housing 20 until the relatively large-diameter portion 88a of sleeve 87 is no longer disposed within enlarged distal portion 24 of slot 22, thereby permitting actuator 84 to be returned proximally. The above-detailed configuration thus permits monopolar assembly 200 to be automatically locked in the deployed condition once the deployed condition is achieved.

Referring to FIGS. 1-5C, the use and operation of forceps 10 in both the bipolar mode, e.g., for grasping, treating and/or cutting tissue, and the monopolar mode, e.g., for electrical/electromechanical tissue treatment, is described. Turning to FIGS. 1 and 2A, with respect to the bipolar mode, initially, actuator 84 is moved to (or remains in) the proximal position at the proximal end of slot 22, corresponding to the un-actuated condition of deployment mechanism 80 and the storage condition of monopolar assembly 200, wherein insulative sleeve 210 is positioned proximally of jaw members 110, 120, and distal tip 224 of energizable rod member 220 is disposed within insulative groove 126 of jaw flange 124 of jaw member 120. At this point, movable handle 40 is disposed in its initial position such that jaw members 110, 120 are disposed in the spaced-apart position. Further, trigger 62 of trigger assembly 60 remains un-actuated such that the knife remains disposed in its retracted position.

Continuing with reference to FIGS. 1 and 2A, with jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 2B. In this approximated position, energy may be supplied, e.g., via activation of switch 4, to plate 112 of jaw member 110 and/or plate 122 of jaw member 120 and conducted through tissue to treat tissue, e.g., to effect a tissue seal or otherwise treat tissue in the bipolar mode of operation. Once tissue treatment is complete (or to cut untreated tissue), the knife may be deployed from within shaft 12 to between jaw members 110, 120, e.g., via actuation of trigger 62 of trigger assembly 60, to cut tissue grasped between jaw members 110, 120.

When tissue cutting is complete, trigger 62 may be released to return the knife to the retracted position. Thereafter, movable handle 40 may be released or returned to its initial position such that jaw members 110, 120 are moved back to the spaced-apart position (FIG. 2A) to release the treated and/or divided tissue.

Referring to FIGS. 1 and 2A-5C, for operation of forceps 10 in the monopolar mode, jaw members 110, 120 are first moved to the approximated position, e.g., by depressing movable handle 40 relative to fixed handle 50. Once the approximated position has been achieved, monopolar assembly 200 may be deployed by transitioning deployment mechanism 80 from the un-actuated condition to the actuated condition. More specifically, in order to deploy monopolar assembly 200, actuator 84 is translated distally along slot 22 and housing 20 from the position shown in FIGS. 3A, 4A, and 5A, through the position shown in FIGS. 3B, 4B, and 5B, to the position shown in FIGS. 3C, 4C, and 5C. This distal translation of actuator 84 urges proximal hub 230 distally relative to housing 20 and shaft 12 and, as a result, moves insulative sleeve 210 and energizable rod member 220 distally from their respective storage positions (FIGS. 2A and 2B) to their respective deployed positions (FIG. 2D). Distal translation of actuator 84 also urges sleeve 87 towards proximal hub 230, against the bias of biasing member 89 due to the non-parallel orientation of the portion 21 of housing 20 relative to the translation axis of proximal hub 230.

Should actuator 84 not reach enlarged distal portion 24 of slot 22, e.g., should deployment mechanism 80 only be transitioned to a partially-actuated condition short of the actuated condition (for example, to the position shown in FIGS. 3B, 4B, and 5B), before being released, biasing member 89 functions to urge actuator 84 proximally, as detailed above, such that deployment mechanism 80 is returned to the un-actuated condition and monopolar assembly 200 is returned to the storage condition. Thus, in order to transition monopolar assembly 200 to the deployed condition and lock monopolar assembly 200 in the deployed condition, actuator 84 needs to be translated to the enlarged distal portion 24 of slot 22. When actuator 84 is translated to the enlarged distal portion 24 of slot 22 (FIGS. 3C, 4C, and 5C), corresponding to the actuated condition of deployment mechanism 80 and the deployed condition of monopolar assembly 200, the relatively large-diameter portion 88a of sleeve 87 is urged under the bias of biasing member 89 at least partially through enlarged distal portion 24 of slot 22 such that actuator 84 is locked in position under the bias of biasing member 89, thereby maintaining deployment mechanism 80 in the actuated condition and locking monopolar assembly 200 in the deployed condition.

With monopolar assembly 200 locked in the deployed condition, activation switch 4 may be actuated to supply energy to energizable rod member 220 to treat, e.g., dissect or otherwise treat, tissue. During application of energy to tissue via energizable rod member 220, forceps 10 may be moved relative to tissue, e.g., longitudinally, transversely, and/or radially, to facilitate electromechanical treatment of tissue. At the completion of tissue treatment, monopolar assembly 200 may be unlocked and returned to the storage condition. In order to return monopolar assembly 200 to the storage condition, actuator 84 is urged towards housing 20 until the relatively large-diameter portion 88*a* of sleeve 87 is no longer disposed within enlarged distal portion 24 of slot 22. Thereafter, actuator 84 may be returned proximally and ultimately released such that actuator 84 is returned to the proximal end of slot 22 under the bias of biasing member 89, thereby returning deployment mechanism 80 to the un-actuated condition (FIGS. 3A, 4A, and 5A), and monopolar assembly 200 to the storage condition (FIGS. 2A and 2B).

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;
an energizable member movable between a storage position and a deployed position;
a proximal hub disposed within the housing and coupled to the energizable member, the proximal hub selectively translatable relative to the housing along a translation axis to move the energizable member between the storage position and the deployed position;
a shaft extending distally from the housing, the shaft having an end effector disposed at a distal end thereof, wherein, in the deployed position, at least a portion of the energizable member extends distally from the end effector assembly;
an insulative sleeve coupled to the proximal hub, wherein translation of the proximal hub along the translation axis moves the insulative sleeve between a storage position and a deployed position, and wherein, in the deployed position, the insulative sleeve is at least partially disposed about the end effector assembly; and
a deployment mechanism configured to selectively translate the proximal hub, the deployment mechanism including:
an actuator movable along a surface of the housing, the surface of the housing extending in non-parallel orientation relative to the translation axis such that the actuator is movable in non-parallel orientation relative to the translation axis, the actuator operably coupled to the proximal hub and movable along the surface of the housing between a proximal position and a distal position to translate the proximal hub along the translation axis and move the energizable member between the storage position and the deployed position.

2. The surgical instrument according to claim 1, wherein the deployment mechanism further includes:
a post extending from the proximal hub in generally perpendicular orientation relative to the translation axis; and
a sleeve slidably disposed about the post, the sleeve having the actuator extending therefrom, wherein the sleeve is slid about the post upon movement of the actuator along the surface of the housing.

3. The surgical instrument according to claim 2, wherein the deployment mechanism further includes a biasing member disposed about the post and positioned between the sleeve and the proximal hub, the biasing member configured to bias the sleeve away from the proximal hub.

4. The surgical instrument according to claim 3, wherein the surface of the housing defines a proximal end and a distal end, the distal end of the surface of the housing disposed in closer proximity to the translation axis as compared to the proximal end of the surface such that the biasing member biases the energizable member towards the storage position.

5. The surgical instrument according to claim 3, wherein at least a portion of the sleeve extends through a slot defined within the housing.

6. The surgical instrument according to claim 5, wherein the slot defines an enlarged portion at an end thereof, the enlarged portion of the slot configured to permit the sleeve to further extend through the slot under the bias of the biasing member to lock the actuator at the end of the slot, thereby locking the energizable member in the deployed condition.

7. The surgical instrument according to claim 1, wherein the end effector assembly includes first and second jaw members, at least one of the first and second jaw members movable relative to the other between a spaced-apart position and an approximated position for grasping tissue therebetween.

8. The surgical instrument according to claim 7, wherein the end effector assembly is adapted to connect to a source of bipolar energy for treating tissue grasped between the first and second jaw members and wherein the energizable member is adapted to connect to a source of monopolar energy for treating tissue adjacent the energizable member.

9. A surgical instrument, comprising:
a housing;
a shaft extending distally from the housing;
an end effector assembly disposed at a distal end of the shaft;
a deployable assembly including an insulative sleeve, an energizable member, and a proximal hub, the deployable assembly transitionable between a storage condition and a deployed condition, wherein, in the deployed condition, the insulative sleeve is at least partially disposed about the end effector assembly and at least a portion of the energizable member extends distally from the end effector assembly, the proximal hub disposed within the housing and coupled to the insulative sleeve and the energizable member, the proximal hub selectively translatable relative to the housing along a translation axis to transition the deployable assembly between the storage condition and the deployed condition; and
an actuator coupled to the proximal hub for selectively deploying the deployable assembly, the actuator movable relative to the housing along a path that extends in non-parallel orientation relative to the translation axis, the actuator movable between an un-actuated position corresponding to the storage condition of the deployable assembly, wherein the actuator is disposed at a proximal end of a portion of the housing and wherein the actuator is spaced-apart from the translation axis a first distance, and an actuated position corresponding to the deployed condition of the deployable assembly, wherein the actuator is disposed at a distal end of the portion of the housing and wherein the actuator is spaced-apart from the translation axis a second distance that is smaller than the first distance.

10. The surgical instrument according to claim 9, further including:
a post extending from the proximal hub; and
a sleeve slidably disposed about the post, the sleeve having the actuator extending therefrom, wherein the sleeve is slid about the post upon movement of the actuator relative to the housing.

11. The surgical instrument according to claim 10, further including a biasing member disposed about the post and positioned between the sleeve and the proximal hub, the biasing member configured to bias the sleeve away from the proximal hub, thereby biasing the actuator towards the un-actuated position.

12. The surgical instrument according to claim 9, wherein the portion of the housing extends in non-parallel orientation relative to the translation axis, and wherein the actuator is slidable along a surface of the portion of the housing.

13. The surgical instrument according to claim 9, further including a lock mechanism configured to lock the actuator in the actuated position corresponding to the deployed condition of the deployable assembly.

14. The surgical instrument according to claim 9, wherein the end effector assembly includes first and second jaw members, at least one of the first and second jaw members movable relative to the other between a spaced-apart position and an approximated position for grasping tissue therebetween.

15. The surgical instrument according to claim 14, wherein the end effector assembly is adapted to connect to a source of bipolar energy for treating tissue grasped between the first and second jaw members and wherein the energizable member is adapted to connect to a source of monopolar energy for treating tissue adjacent the energizable member.

* * * * *